(12) United States Patent
Bauer

(10) Patent No.: US 12,419,506 B2
(45) Date of Patent: Sep. 23, 2025

(54) OPTICAL FILTER FOR AN OBJECTIVE SYSTEM OF AN ENDOSCOPE, OBJECTIVE SYSTEM, AND ENDOSCOPE

(71) Applicant: KARL STORZ SE & Co KG, Tuttlingen (DE)

(72) Inventor: Franz Bauer, Tuttlingen (DE)

(73) Assignee: KARL STORZ SE & Co KG, Tuttlingen (DE)

( * ) Notice: Subject to any disclaimer, the term of this patent is extended or adjusted under 35 U.S.C. 154(b) by 445 days.

(21) Appl. No.: 18/073,305

(22) Filed: Dec. 1, 2022

(65) Prior Publication Data

US 2023/0172444 A1 Jun. 8, 2023

(30) Foreign Application Priority Data

Dec. 8, 2021 (DE) .......................... 102021132233.2

(51) Int. Cl.
*A61B 1/04* (2006.01)
*A61B 1/06* (2006.01)

(52) U.S. Cl.
CPC ............ *A61B 1/043* (2013.01); *A61B 1/0638* (2013.01)

(58) Field of Classification Search
CPC ... A61B 1/043; A61B 1/0638; A61B 1/00186; A61B 1/0605; A61B 1/0607; A61B 1/0627; A61B 1/0646
See application file for complete search history.

(56) References Cited

U.S. PATENT DOCUMENTS

| 5,943,129 | A | * | 8/1999 | Hoyt | G01N 21/6456 356/417 |
|---|---|---|---|---|---|
| 5,980,454 | A | * | 11/1999 | Broome | A61B 1/05 359/615 |
| 6,248,060 | B1 | * | 6/2001 | Buess | A61B 1/00165 600/177 |
| 9,885,859 | B2 | * | 2/2018 | Harris | G02B 21/367 |
| 2003/0164952 | A1 | * | 9/2003 | Deichmann | B33Y 50/00 356/603 |
| 2008/0269563 | A1 | * | 10/2008 | Takahashi | G02B 23/2461 600/178 |
| 2010/0020333 | A1 | * | 1/2010 | Kunz | G02B 23/2461 359/709 |
| 2012/0248333 | A1 | * | 10/2012 | Fallert | G01N 21/6456 250/208.1 |

(Continued)

*Primary Examiner* — Anh Tuan T Nguyen
*Assistant Examiner* — Jae Woo
(74) *Attorney, Agent, or Firm* — David N. Villalpando; Jacqueline Cohen

(57) ABSTRACT

An objective system of a medical scope including an optical filter is disclosed. The optical filter includes a light incident side and a light exit side, a central region around an optical axis, and a peripheral region and is designed as an aperture with a single optical axis for white light and fluorescence light. The optical filter includes a first transmission zone for a transmittance of a first wavelength band and a second transmission zone for a transmittance of a second wavelength band at least partially different from the first wavelength band. At least one of the two transmission zones includes a filter coating. As a result, when both white light and fluorescence light pass the optical filter, a light beam cone of the fluorescence light has a larger diameter than a light beam cone of white light or vice versa. The invention also discloses a related endoscope.

20 Claims, 3 Drawing Sheets

(56) References Cited

U.S. PATENT DOCUMENTS

2019/0142257 A1* 5/2019 Vinther .................. A61B 1/227
                                                      600/200
2024/0094518 A1* 3/2024 Deissler ............. G02B 21/0076
2024/0280490 A1* 8/2024 Perry .................. G02B 21/0032
2024/0362883 A1* 10/2024 Deliwala .............. A61B 5/0075

* cited by examiner

OPTICAL FILTER FOR AN OBJECTIVE SYSTEM OF AN ENDOSCOPE, OBJECTIVE SYSTEM, AND ENDOSCOPE

CROSS REFERENCE TO RELATED APPLICATIONS

This application claims priority to German Patent Application No. 102021132233.2, filed Dec. 8, 2021, and entitled, "Optical Filter for an Objective System of an Endoscope, Objective System and Endoscope," which is incorporated herein by reference.

FIELD OF THE INVENTION

The invention concerns an optical filter for an objective system of a medical scope, wherein the optical filter comprises a light incident side and a light exit side, a central region around an optical axis and a peripheral region, wherein the optical filter is designed as an aperture with a single optical axis for white light and fluorescence light. Furthermore, the invention concerns an objective system and an endoscope.

BACKGROUND OF THE INVENTION

Endoscopes for use in medical and non-medical applications may utilize both white light and fluorescence imaging. Endoscopic instruments intended for industrial use, rather than medical use, are often referred to as borescopes. As this invention relates to both medical endoscopes and borescopes, the term "endoscope" is used to generally include both instruments. Conventional endoscopes that are able to capture both fluorescence and white light images with a single optical path have an identical F-number across the entire wavelength spectrum. This usually results in significantly less fluorescence illumination intensity being detected by the image sensor than from the corresponding white light illumination insofar as fluorophore emission radiation is usually only a small fraction of the corresponding white light collected by the endoscopic optical system. This results in lower sensitivity in the fluorescence range as well as reduced resolution of the fluorescence image compared to the white light image. As the optical paths for the white light image and the fluorescent image in conventional systems have the same aperture size, and therefore the same F-number over all spectral ranges, the resulting white light image has a shorter depth of field than could be achievable had it been possible to use a smaller aperture.

A known multi-region filter is described, for example, in U.S. Pat. No. 4,801,792 A, wherein an endoscope comprises a two-region annular electronically controlled aperture with a light transmitting section disposed along an optical axis of the objective lens unit and a variable light transmitting section surrounding the light transmitting section capable of being changed between a light transmitting state and a light blocking state, in order to obtain a desired depth of field and brightness. Fluorescence imaging is not considered by U.S. Pat. No. 4,801,792 A.

U.S. Pat. No. 10,324,300 B2 discloses an imaging head for an endoscope, wherein unpolarized image light passes an annular polarizing aperture resulting in a first polarized beam with a first F-number and a second beam with a second F-number. The first beam corresponding to the first F-number is split by means of a polarizing beam splitter on one image sensor and the second beam with the second F-number on a second image sensor, wherein the images are subsequently combined by image processing to achieve a resulting image with a higher resolution in a region of interest and an overall larger depth of field. However, hereby always a loss of light and therewith a loss of intensity occurs due to polarization beamsplitter distributing beams of light with different polarization. Consequently, the teaching of U.S. Pat. No. 10,324,300 B2 is not applicable for the simultaneous imaging of white light and fluorescence light along a single optical path due to the significant loss of light intensity due to the polarization filters, which is of particular concern to the detection of weak fluorescence signals.

US 2003/0202252 A1 discloses a machine vision system for inspecting of semiconductor chip bonding devices with a light source, a beamsplitter for receiving an image of the device illuminated by the light source, wherein the beamsplitter providing one of the plurality of images of the device based in a wavelength of the light source, and with an aperture having a plurality of effective diameters based on the wavelength of light from the light source and determining a depth of field of the image of the device, and an optical element for receiving the image of the device and magnifying the image. The light has a wavelength within the visible and/or UV spectrum.

In the patent application DE 10 2021 106 836.3 by the present Applicant, KARL STORZ SE & Co. KG, an optical filter system for a video endoscope is described comprising an optical filter with a varying transmission characteristic placed within the objective lens system, on the distal side of the objective lens system in front of the system aperture. The filter system permits the overlaying of fluorescence and visible light image data, overcoming problems associated with the diverging angles of incidence at the filter surface that are particularly relevant for short optical systems.

BRIEF DESCRIPTION OF THE INVENTION

Problems in the state-of-the-art associated with a single F-number being used for both fluorescence and visible light imaging, and the resulting limitations in light gathering capabilities for the two signals, is solved by an optical filter for an objective system of a medical scope, wherein the optical filter comprises a light incident side and a light exit side, a central region around an optical axis and a peripheral region, wherein the optical filter is designed as an aperture with a single optical axis for white light and fluorescence light, wherein the optical filter comprises at least a first transmission zone for a transmittance of a first wavelength band and a second transmission zone for transmittance of a second wavelength band, wherein at least one of the two transmission zones comprises a filter coating and the first wavelength band and the second wavelength band differ at least partially from each other, so that in case of both white light and fluorescence light, the optical filter results in a light beam cone of the fluorescence light having a larger diameter than a light beam cone of the white light or vice versa.

Thus, the known limitation of conventional medical scopes, such as endoscopes, that use the same optical channel for both white light and fluorescence imaging is overcome by providing an independent F-number for a first wavelength band, for example white light, and a separate, distinct and/or smaller F-number for a second wavelength band, such as for fluorescence imaging, by means of the optical filter being designed as a dual diameter aperture. This results in a beam of the second wavelength band wider than the beam of the first wavelength band. Thus, in case of fluorescence imaging this, in turn, results in more fluorescence illumination passing through the single optical channel to an image sensor, resulting in the capture of a brighter and higher resolution image than would be possible with an aperture with a larger F-number. Additionally, a narrower aperture opening results in a wider depth of field for light captured in the first wavelength band, such as in the visible spectrum. Another benefit of the present invention is that an optimal tuning of the F-number ratio for a given design can maximize the brightness of the fluorescence image relative to the necessary white light intensity. Consequently, for the fluorescence wavelength band, the depth of field and the resolution requirements are adapted to match the requirements of the image of the white light band. That is, one can tune the F-numbers for each wavelength band and/or by each transmission zone, coupled with the illumination intensity and image sensor exposure characteristics in order to maximize image quality for both fluorescence and white light imaging.

Therewith, the image brightness of a defined spectrum range can be increased without necessarily influencing the optical parameters in another spectral range by selecting an appropriate aperture size ratio for each wavelength band. Therewith by using a larger aperture diameter and transmission zone only for the second wavelength band, such as for fluorescence imaging, the depth of field of the first wavelength band, e.g., white light, is not affected and not lost. Thus, in general the optical filter works as an aperture with different diameters of transmission zones and/or blocking zones for each spectral range of interest.

It is especially advantageous that, by using the present optical filter within the single channel objective system of a medical scope, the same or almost the same optical resolution can be achieved for white light and fluorescence light images, by selecting an advantageous ratio of sizes and/or diameters of the two transmission zone, while maintaining a desired depth of field of the white light image. Again, this can be done by selecting an appropriate F-number for the white light, in order to achieve the desired depth of field of the visual image, given a specific illumination intensity of the viewed scene, and selecting a F-number for the fluorescence light as a ratio of that of the white light.

In another embodiment of the invention, the optical filter comprises a blocking zone, wherein the blocking zone is arranged at and/or in the peripheral region of the optical filter for blocking of light of all wavelengths.

Therefore, the outer blocking zone serves as a blocking element for white light as well as fluorescence light and defines the outer maximally possible diameter for beams of white light and fluorescence light incident on the optical filter. The blocking zone with its inner opening serves as an aperture for the passing of fluorescence light.

For the exclusive transmittance of fluorescence light, the second transmission zone can be arranged between the peripheral region and the central region of the optical filter for blocking of white light and transmittance of fluorescence light.

In a further embodiment of the invention, the first transmission zone is arranged in the central region of the optical filter for transmittance of white light and/or fluorescence light.

Therefore, the second transmission zone as an aperture stop with its blocking of white light over its cross-sectional area, serves in combination with the first transmission zone as an aperture opening for the white light passing therethrough.

Therewith, the first transmission zone can be simply designed as an aperture opening in the central region of the optical filter without any filter coating, allowing the transmittance of white light and fluorescence light. As a result, a loss from the glass reflection of the optical filter of about 5% in all spectral ranges may occur.

In order to implement a specific filtering function based on the wavelength and/or wavelength bands, the first transmission zone, the second transmission zone and/or the blocking zone comprises or comprise a respective filter coating.

Therefore, the specific blocking and/or transmittance of light of certain wavelength bands can be adapted and controlled by each respective filter coating of each transmission zone.

Preferably, the first transmission zone comprises a wide range coating in the center region for transmittance of both wavelength ranges, e.g. of white light and fluorescence light, and the second transmission zone comprises a reflecting coating for white light and a diameter and therewith an opening that provides a smaller F-number for the specific wavelength band of fluorescence light. Additionally, the angle of incidence in the first transmission zone can be lowered by the filter coating, which facilitates the design of the optical filter.

In yet another embodiment of the optical filter, the blocking zone comprises a black filter coating or is formed as a ring element at the light incident side.

Consequently, by the black filter coating or the ring element all wavelengths can be completely blocked.

A "ring element" is in particular any kind of ring-shaped body or component that is arranged at the light incident side before or at the preferably planar surface of the filter element in the peripheral region. The ring element can have a circular, square, hexagonal or any suitable basic form.

Depending on the fabrication of the optical filter, the respective filter coating or the respective filter coatings of the first transmission zone, the second transmission zone and/or the blocking zone is or are arranged on the light incident side and/or the light exit side.

For example, all filter coatings can be arranged on the light incident side of the filter, each joined together with it edge to the adjacent edge of the next filter coating. Alternatively, one or more filter coatings can also be arranged on the light exit side. For example, the filter coatings can be arranged alternately from the central region to the peripheral region on the light incident side and the light exit side. By this design, the adjacent filter coatings in the direction from the center to the peripheral region do not have to be joined exactly at their edges, facilitating the filter manufacture. Instead, due to the alternating arrangement on the incident side and subsequently on the exit side, the adjacent filter coatings can overlap relative to each other on both sides. Furthermore, by locating and splitting both transmissions zones and/or the blocking zone either to the light incident side or the light exit side, the aperture for each wavelength band is not arranged on the same surface, but divided on the front side and backside of the optical filter.

In another embodiment of the optical filter, the second transmission zone for transmission of fluorescence light comprises a F-number in a range between F/3.5 to F/4.5 and/or the first transmission zone for transmission of white light comprises a F-number in a range between F/5.5 to F/6.5.

Therewith, simultaneously the required criteria of a large depth of field for the white light and an improved illumination, brightness and resolution for the fluorescence light are met. As, in general, the resolution decreases with increasing wavelength, the resolution of a white light spectrum with, for example, a F-number of 6 corresponds to a fluorescence spectrum with, for example, a F-number of 4 in its resolution.

In a further embodiment of the optical filter, the second transmission zone for transmission of fluorescence light comprises an outer diameter in a range between 0.85 mm to 1.25 mm and/or the first transmission zone for transmission of white light and/or fluorescence light comprises an outer diameter in a range between 0.60 mm to 0.85 mm.

For blocking almost all light across wavelength bands, the filter coating of the blocking zone comprises a transmission of less than 0.01% in the wavelength band of 350 nm to 1,100 nm.

For allowing the passing of fluorescence light, in particular the emission wavelength or wavelength band of the fluorophore, and simultaneously for an almost complete blocking of white light, the filter coating of the second transmission zone comprises a transmission of more than 98.0% in the wavelength band of 800 nm to 900 nm and a blocking of more than 99.5% in the wavelength band of 400 nm to 750 nm.

In a further embodiment of the optical filter, the filter coating of the first transmission zone comprises a blocking of less than 2.5%, preferably less than 1.2%, in the wavelength band of 415 nm to 900 nm.

Consequently, simultaneously most of the white light and the fluorescence light can pass the filter coating of the first transmission zone in the central region of the optical filter.

In a further aspect of the invention, the problem is solved by an objective system for an endoscope, wherein the objective system is arrangeable in a distal end section of an elongate shaft of the endoscope and at least a first image sensor for receiving image light is arranged in an image plane or in the distal end section, wherein the objective system comprises an objective lens system with a first lens, a second lens, a third lens and/or further lenses in order from an object side to receive image light and to pass the image light towards the at least first image sensor, wherein the objective system comprises one optical channel for white light and fluorescence light, and the objective system comprises an optical filter as previously described, so that white light and fluorescence light with different corresponding F-numbers are capturable by the at least first image sensor.

Thus, an objective system for an endoscope is provided with just one and the same optical channel for both white light and fluorescence light imaging, wherein, by the optical filter designed as an aperture, different aperture openings with different wavelength dependent transmissibility and different outer beam diameters are provided for white light and fluorescence light for optimal imaging by the image sensor.

For separating the excitation wavelength used for excitation of the fluorophore, the objective system comprises a fluorescence filter for blocking of an excitation wavelength, wherein the fluorescence filter is arranged on a proximal side of the optical filter within the objective system.

Therewith, a conventional fluorescence filter is arranged on the proximal side of the optical filter. Alternatively, the optical filter can also include the fluorescence filter, so that only fluorescence light of the emission wavelength or wavelength band of the respective fluorophore passes the optical filter. In this case, the second transmission zone and the first transmission zone comprise each a filter coating which simultaneously blocks the excitation wavelength of the fluorophore.

In a further aspect of the invention, the problem is solved by an endoscope, in particular medical or industrial video endoscope, with a handle, an elongate shaft, a light source, an objective system and/or a display system, wherein the objective system of the endoscope comprises an optical filter as previously described or the objective system is an objective system as previously described, so that white light and fluorescence light are displayed by means of the display system with an approximately same resolution.

Instead of an endoscope, certainly the objective system with the optical filter can also be used in a camera or camera head.

BRIEF DESCRIPTION OF THE DRAWINGS

The invention is further explained by the following exemplary description of particular embodiment. The figures show.

DETAILED DESCRIPTION OF THE INVENTION

Figure 1:
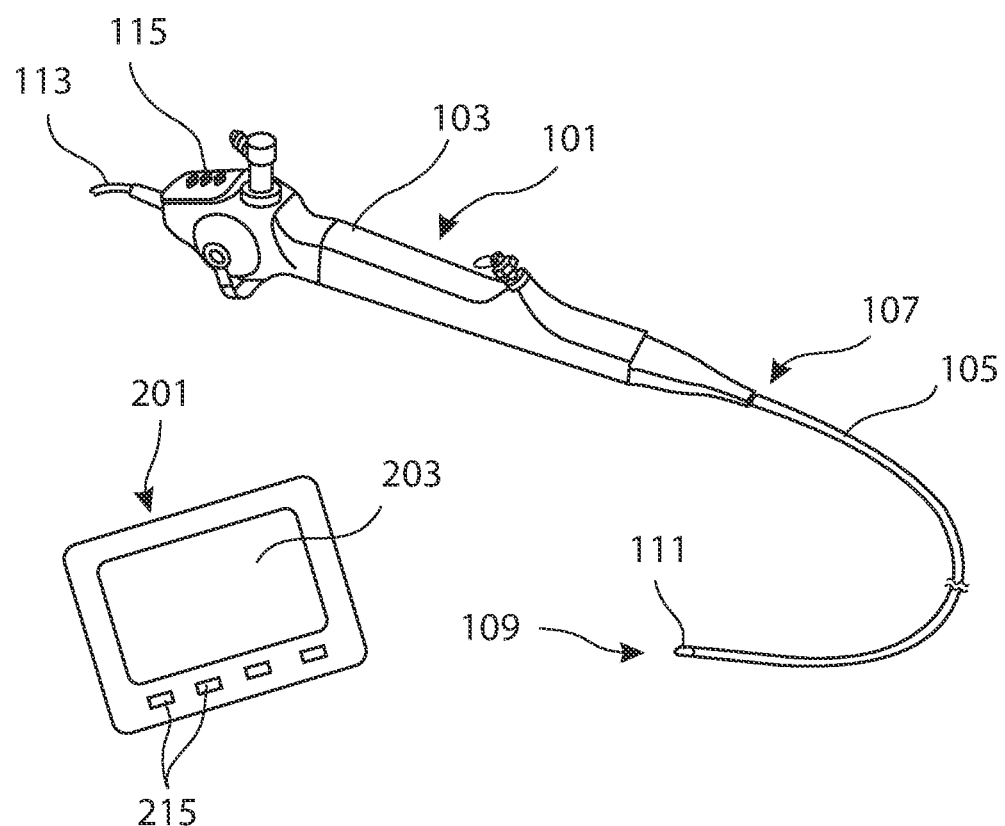
FIG. 1 a schematic partially three-dimensional view of an endoscope and a display system.

One of the primary ideas of the invention is the special design of an optical filter as one aperture with at least two different aperture stops and/or transmission zones with blocking (generally by reflection but can also be by absorption or other method of retardance) and/or transmission properties based on wavelength bands and thereby providing two differently dimensioned aperture openings for different wavelength bands in order to achieve a larger aperture opening and therefore a larger diameter for fluorescence light beams relative to the diameter for white light in the same optical path. This differentiation by transmitting in two different wavelength bands by means of the optical filter is in contrast to the common approach and design of objective systems, where different optical properties are neither desired nor realized in a single optical system.

It is especially advantageous that the optical filter is positioned within the objective system at a position where it simultaneously provides blocking and transmission depending on the wavelength band and serves as one aperture with at least two different aperture stops for the objective system. Hereby, the optical filter is placed in the aperture plane of the objective system.

As utilized in accordance with the present disclosure, the following terms, unless otherwise indicated, shall be understood to have the following meanings.

An "optical filter" is, in particular, an optical element which selects the incident radiation and/or rays based on the specific wavelength and therefore frequency. The optical filter comprises at least two different transmission zones and therewith two different aperture stops for blocking and/or transmittance of at least two different wavelength bands. In particular, at least one of the at least two transmission zones and/or aperture stops comprises a filter coating, which is wavelength selective. Therewith, the filter coating effects a blocking or transmission of the respective light incident on the optical filter depending on its wavelength. In particular, the optical filter provides two different aperture opening sizes, one for the first wavelength band, such as white light, and a distinct aperture opening size for the second wavelength band, such as fluorescence light. Certainly, the optical filter can also comprise three or more transmission zones for transmittance of at least partially different wavelength bands. Furthermore, in a design with multiple transmission zones, also two transmission zones, which are not directly adjacent to each other, may transmit the same wavelength band. The optical filter preferably comprises glass and/or a crystalline material. The optical filter can be used as an observation and/or detection filter within the objective system.

The optical filter is preferably circular from its central region around its central point to a peripheral region or rim. The optical filter is planar on the objective side, which is the light incident side, as well as on the light exit side, which is the side directed towards the image sensor. In the view direction along the optical axis, the optical filter can have an annular, rectangular or square cross section for the light to pass therethrough or any other suitable form. Preferably, the center region and/or the center point of the optical filter is co-linear with the optical axis. The "central region" is the region around the center point and/or the optical axis of the optical filter. The "peripheral region" is the region within the outer edge and/or outside the outer edge of the optical filter.

The "optical axis" is, in particular, a line along which some degree of rotational symmetry exists in an optical system. The optical axis is in particular in an imaginary line that defines the path along which light propagates through the optical filter and the objective system towards the image sensor. Preferably, the optical axis passes through the center of curvature of each optical element and/or filter within the lens system and/or objective system. However, the optical axis can also be bent and/or directed by a lens, an optical element and/or the optical filter.

A "medical scope" is in particular any kind of scope and therewith any optical instrument usable for medical applications. A medical scope is for example an exoscope or an endoscope. While in the following the invention is described for an endoscope, the invention is likewise applicable for and in an exoscope.

A "transmission zone" is in particular an area on and/or in the optical filter, through which light of a certain wavelength band can pass along the single optical axis. The transmission zone forms in particular part of the cross-section area of the optical filter. In the cross section view the transmission zone can be arranged with a certain inner diameter and/or outer diameter from the center point and therewith from the optical axis and/or around the axis. In case of a circular optical filter in the cross-section view, the inner transmission zone is circular and in the radial direction towards the peripheral region the following transmission zone is ring-shaped.

An "aperture" is an optical element which limits the cross-section of bundles of rays and/or the maximum diameter of light beams. The aperture comprises a hole or an opening through which light travels. In particular, the aperture and focal length of an optical system determines the cone angle of a bundle of rays that come to a focus in the image plane. The aperture in particular comprises an aperture stop primarily determining the ray cone angle and the brightness of the image point, and, in case of the aperture stop and/or transmission zone comprising a filter coating, determines the blocking by absorption or reflection or the transmittance of light depending on its wavelength band. Thus, a transmission zone and/or an aperture stop comprising a filter coating deposited on its cross-sectional area works simultaneously as a blocking element for the blocking of light within a certain predetermined wavelength band and as an open passage for the transmittance of light within a different wavelength band.

Under "the first wavelength band and the second wavelength band differ at least partially from each other" is understood that the first wavelength band and the second wavelength band do not include exactly the same wavelengths. However, the first wavelength band may include completely the second wavelength band or vice versa. For example, the first wavelength band comprises the wavelength range of 400 nm to 900 nm and the second wavelength band comprises the wavelength range of 700 nm to 800 nm.

"White light" (also called "visible light") is usually understood to refer to a combination wavelengths of light at from 380 nm to 750 nm, that is between the ultraviolet and infrared regions, that is, electromagnetic radiation within the portion of the spectrum perceived by the human eye.

"Fluorescence" is in particular an emission of light by a substance called a fluorophore that has absorbed light or other magnetic radiation. The fluorophore is usually irradiated with a specific excitation wavelength or wavelength band resulting in the emission of light with a specific emission wavelength or wavelength band. Normally, the emission wavelength is longer than the excitation wavelength. For example, in case of the commonly used fluorophore indocyanine green (ICG), the excitation wavelength range is between 600 nm and 900 nm and the emission wavelength range is between 750 nm and 950 nm in the IR spectrum. In fluorescence imaging, which is often used to optically define a tumorous region during surgery, a biological material, such a tissue in a body cavity is dyed with a fluorophore directly, or an administered substance is converted into a fluorophore by the body or a microorganism prior to imaging with a medical scope, e.g., endoscope or exoscope. Additionally, auto fluorescence can also be observed without previous colorization by a fluorophore or dye.

Consequently, "fluorescence light" may refer to the excitation and/or emission wavelengths or wavelength bands of a fluorophore. In fluorescence imaging, an optical filter, such as that of the present invention, or a conventional fluorescence filter blocks the excitation wavelength from reaching the detecting image sensor, and therefore the fluorescence light comprises only the light emitted by the fluorophore.

An "objective system" is an optical system which includes one optical filter, an objective lens system to receive, pass forward and modify the image light from an objective field, and at least one image sensor for capturing the image. The objective system can be part of a camera or a camera head of an endoscope.

An "objective lens system" comprises in particular, in an order from an object side, a cover glass and/or a first lens, a second lens and/or further lenses, which are arranged along an optical axis of the lens system. The optical filter can be located between two lenses of the lens system at a position where the optical filter serves simultaneously as the aperture of the whole objective lens system.

A "lens" is in particular a transmissive optical body that focusses or disperses a light beam (light rays) by means of refraction. The first lens, the second lens, the third lens and further lenses can be single lenses, which are separated by an air gap or are in contact to adjacent lenses at most pointwise. Also, a lens can be a combined lens or a rod lens. Preferably, the lenses are made of glass and/or a crystalline material.

An "endoscope", in particular a video endoscope, is an endoscope with a means for digital image acquisition at the distal end of the elongate shaft, and the transmission of data therefrom, for example to the proximal end of the endoscope. The endoscope comprises an elongate shaft and a handle which are connectable to each other. At least one digital image sensor is located at the distal end of the elongate shaft for image acquisition. In particular, the video endoscope is any kind of digital endoscope, for example a 2D colonoscope or gastroenteroscope or a 3D video endoscope. The endoscope can comprise or be connected to a camera or a camera head.

The "elongate shaft" is in particular a rigid, semi-flexible or flexible tube. In particular, the shaft is configured for being inserted into a cavity to be viewed endoscopically, for example a body cavity of a human or animal body. In industrial applications, the endoscope, or borescope, shaft will be placed into an element such as a pipe. Generally, the shaft may have an outer diameter in the range of 4 mm to 10 mm. Besides the objective system and one or more image sensors, the shaft may comprise one or more channels for irrigation or passing through working instruments (generally referred to as "working channels") in order to achieve the desired effect in the cavity or opening. The shaft can be detachably connected at its proximal end to a handle or be permanently connected thereto. The distal end section of the elongate shaft is the section remote from the user, while the proximal end section of the shaft is closer to the user.

An "image sensor" has in particular its sensor plane in an image plane of the objective system and/or lens system. The image sensor, in particular an electronic image sensor, may be, for example, a charge-coupled device (CCD) or a complementary metal-oxide semiconductor (CMOS). Preferably, the electronic image sensor is a high-definition (HD) image sensor having, for example, full HD resolution. In general, the electronic image sensor is configured to convert the captured image into electrical image signals and therefore image data. In particular, the electronic image sensor is arranged in the distal end section, e. g. the tip of the shaft, and transmits the electrical image signals from the distal end of the shaft to its proximal end by electric transmission lines, such as wires, cables and/or a flexible printed circuit board. Preferably the electric image signals generated by the electronic image sensor are transferred from the shaft to the handle of the endoscope and/or a display system and/or a processing unit for displaying the captured images. Alternatively, the image sensor is arranged at the proximal side of the endoscope and the collected image light is relayed proximally by known means such as rod lenses or optical fibers.

A video endoscope 101 comprises a handle 103 and an elongate shaft 105 connectable to each other at a proximal end 107 of the shaft 105. The handle 103 comprises operator controls 115 and is connected via a cable 113 at its proximal end to an external, non-shown control and processing unit and to a display system 201 shown in FIG. 1. The display system 201 includes a monitor 203 for displaying endoscopic images and operator controls 215.

The video endoscope 101 is designed to provide video and image data from an objective field within a cavity of a non-shown body. For this, the elongate shaft 105 comprises at its distal end 109 a distal end section 111.

The distal end section 111 of the elongate shaft 105 comprises an objective system 301 with an optical filter 311 designed as the aperture of the objective system 301. The optical filter 311 comprises an outer ring 313 at its peripheral region 377, which blocks all radiation in the entire wavelength range and serves as an aperture for the fluorescence spectral range of a fluorophore, such as ICG. Between the outer ring 313, as a first aperture stop, and a central region 375 is a middle ring coating 315 for absorbtion of white light and transmission of fluorescence light. Therefore, the middle ring coating 315 defines an inner radius that serves as an aperture for white light, being the second aperture stop, as well as being a transmission zone for fluorescence light. In the central region 375, an inner ring coating 317, such as an anti-reflection coating, is arranged for transmission of white light and fluorescence light (see FIG. 2). In an alternative not shown in FIG. 2, the optical filter 311 comprises no inner ring coating 317 resulting in a slight intensity loss due to glass reflection by the optical filter 311 itself.

Figure 2:
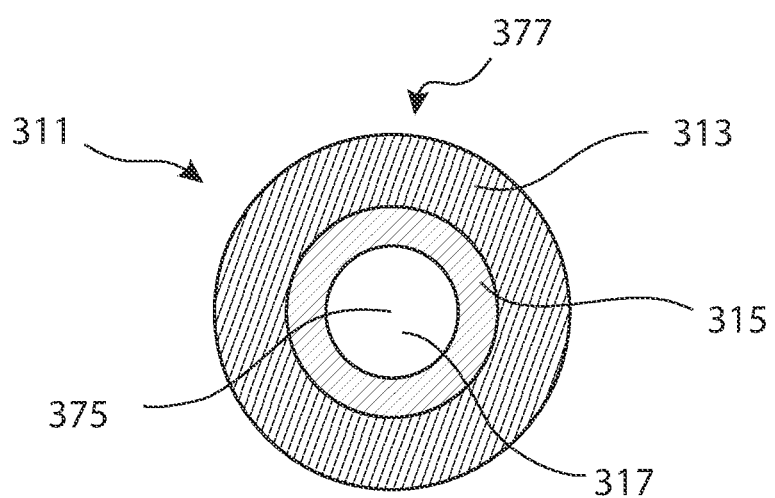
FIG. 2 a schematic cross-sectional view on the incidence light side of an optical filter designed as an aperture.
Figure 3:
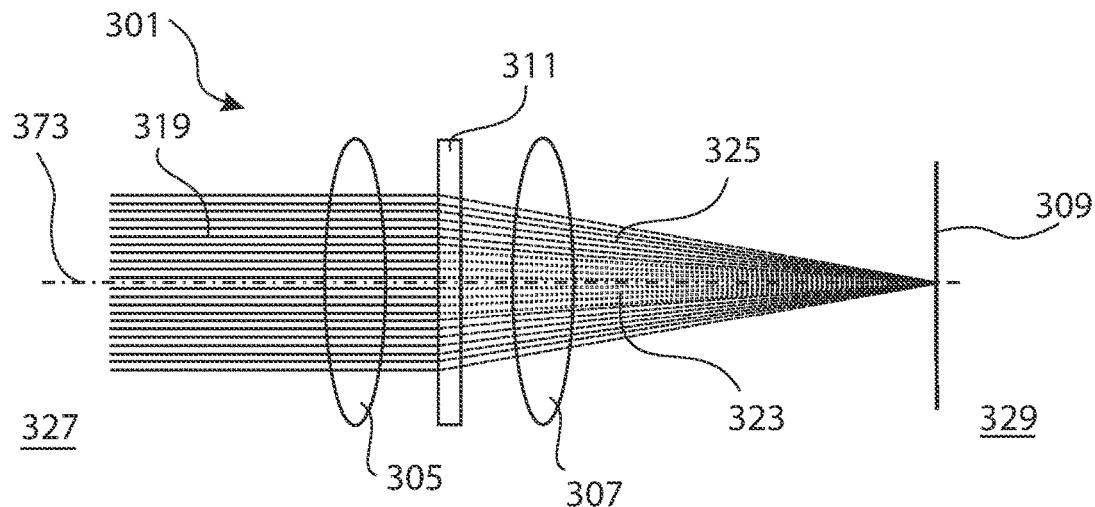
FIG. 3 a presentation of a principal design of a simple objective system.

Corresponding to the design of the optical filter 311 as one aperture shown in FIG. 2, the principal arrangement of a simple objective system 301 is shown in FIG. 3. The objective system 301 comprises, from the distal side 327 along an optical axis 373, a front lens 305 and a rear lens 307, wherein the optical filter 311 is arranged between the front lens 305 and the rear lens 307. The front lens 305 and the rear lens 307 are representative examples for a potentially more complex lens system comprising several lenses such as those shown in FIG. 4. At a proximal side 329, the objective system 301 comprises an image sensor 309.

The light 319 coming from the objective field at the distal side 327 is directed by the front lens 305 (the specific direction of the light beams by the front lens 305 is not shown in FIG. 3) and passed through the optical filter 311. Due to the design of the optical filter 311 as one aperture with the outer ring 313, the middle ring coating 315 and the inner ring coating 317, the fluorescence beam 325 transmitted by the middle ring coating 315 and the inner ring coating 317 has a larger outer diameter than the white light beam 323 only transmitted by the inner ring coating 317. Consequently, different effective diameters for the fluorescence beam 325 and white light beam 323 are achieved. The larger fluorescence beam 325 could, for example, have a F-number of f/4 and the white light beam 323 would have a higher F-number of f/6, and both beams are captured by the image sensor 309. Therefore, the fluorescence beam 325 has enhanced illumination and brightness available for the fluorescence image, while the depth of field of the white light is not changed. Furthermore, the resolution of the longer wavelength, e.g. emission fluorescence light, is adapted to the resolution of the white light for the overlay.

Figure 4:
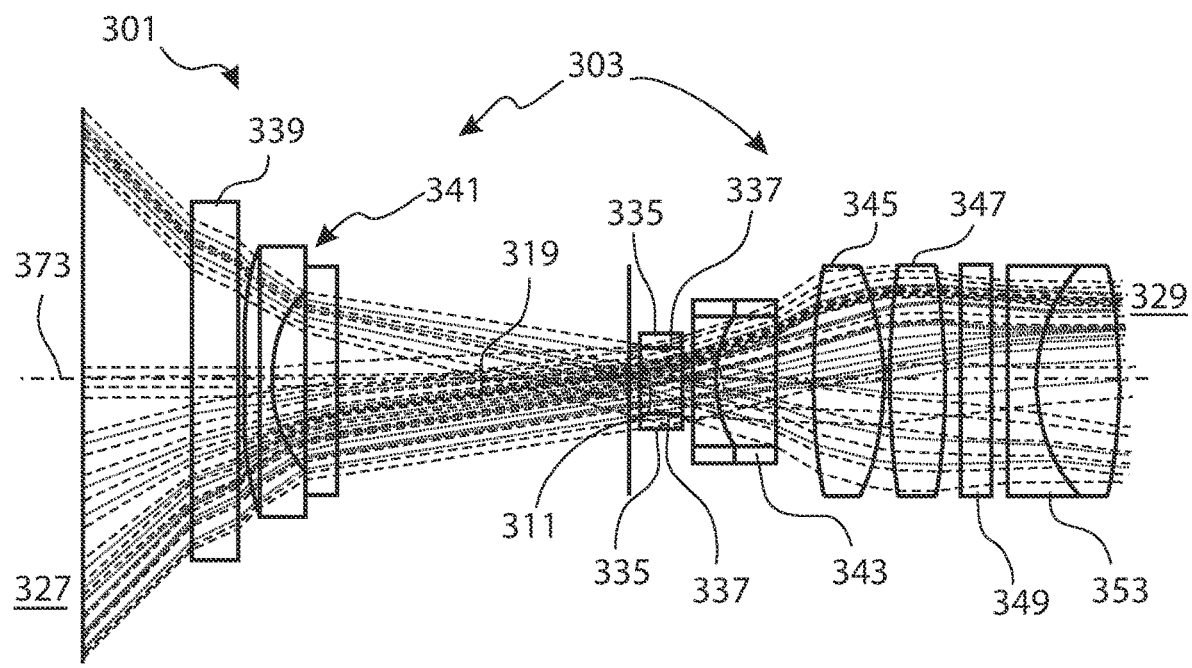
FIG. 4 a schematic sectional view of an objective system with an optical filter as an aperture and a conventional fluorescence filter.

A practical design of an objective system 301 is shown in FIG. 4. The objective system 301 comprises a lens system 303 and an image sensor 309. The lens system 303 comprises, along the optical axis 373 from the distal side 327 towards the proximal side 329, a cover glass 339, followed by a first lens 341 formed as a combined lens, the optical filter 311 followed by a second lens 343 formed as a combined lens, a third lens 345, a fourth lens 347 and a conventional fluorescence filter 349 arranged between the fourth lens 347 and a following fifth lens 353, formed as a combined lens.

As shown in FIG. 4, the optical filter 311 comprises a wider aperture opening 335 due to the filter coating as described above for the fluorescent path and a smaller aperture opening 337 for transmission of white light. The wider fluorescence beams, comprising excitation and emission fluorescence light, passing the aperture opening 335 are filtered by the conventional fluorescence filter 349, which absorbs the excitation wavelength of the fluorescence path and only passes the emission wavelength band of the fluorophore. Subsequently the emission fluorescence beam and the white light beam can be transmitted further to a not shown image sensor as described above.

Figure 5:
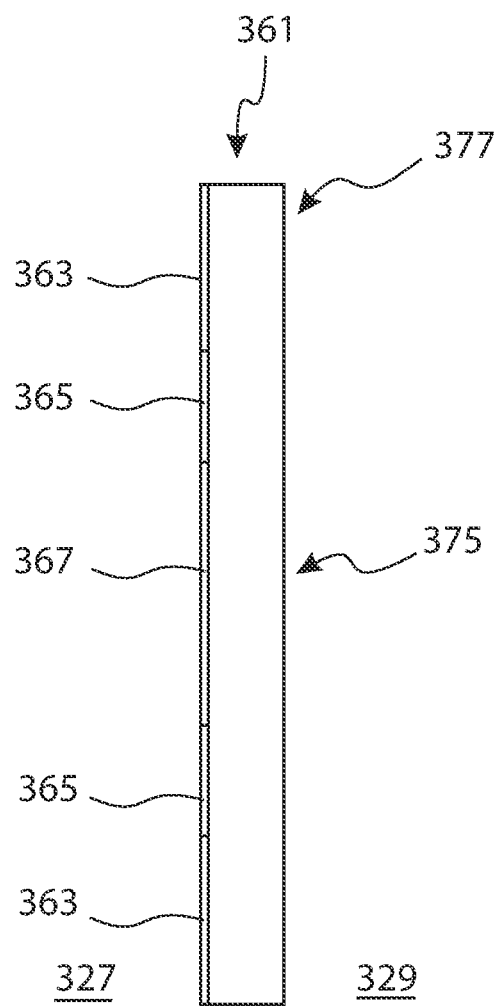
FIG. 5 a cross-sectional view of a one-sided optical filter.
Figure 6:
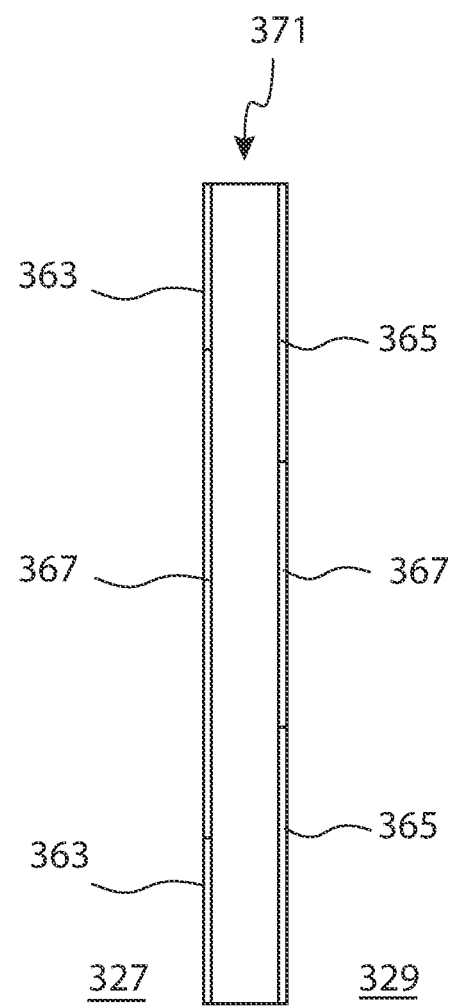
FIG. 6 a cross-sectional view of a double-sided optical filter.

In general, the optical filter 311 can be designed as a one-sided coated optical filter 361 as shown in FIG. 5 or a double-sided optical filter 371 as shown in FIG. 6. In case of the one-sided coated optical filter 361, a black coating 363 is arranged on the light incident side of the one-sided coated optical filter 361 directed towards the distal side 327 to block light of the entire wavelength band as a first aperture stop. Likewise, a reflecting or absorbing coating 365 is arranged between the black coating 363 and the central region 375 of the one-sided coated optical filter 361. The coating 365 is designed as the second aperture stop, which blocks the white light and transmits fluorescence light. In the central region 375, a wide-range coating 367, such as an anti-reflection coating, acts as the third aperture stop and transmission zone allowing the transmission of white light and fluorescence light, and is arranged in the incident side.

In the double-sided optical filter 371 shown in FIG. 6, the black coating 363 in the peripheral region 377 and the wide-range coating 367 are arranged on the light incident side directed towards the distal side 327, while on the light exit side directed towards the proximal side 329 the reflecting coating 365 and the wide-range coating 377 are arranged. The second aperture stop for passing the fluorescence light is formed by the inner edge of the black coating 363 directed towards the distal side 327 and the lower, inner edge of the reflecting coating 365 arranged on the light exit side of the double-sided optical filter 371, while the aperture opening of the third aperture stop is limited by the wide-range coating 367 arranged on the light exit side towards the proximal side 329. The respective coatings 363, 365 and 367 may be applied by lithography on the glass body of the optical filters 361, 371. It should be noted that, while the direction of the filter 371 as shown in FIG. 6 is preferred, other embodiments of the invention could have the filter direction reversed.

Therewith, an optical filter and an objective system are provided for an endoscope, wherein the optical filter is designed as one aperture with at least two different transmission zones and/or aperture stops for filtering fluorescence light and white light, and allowing different F-numbers for fluorescence light and white light.

Although the invention and its advantages have been described in detail, it should be understood that various changes, substitutions and alterations can be made herein without departing from the scope of the invention as defined by the appended claims. The combinations of features described herein should not be interpreted to be limiting, and the features herein may be used in any working combination or sub-combination according to the invention. This description should therefore be interpreted as providing written support, under U.S. patent law and any relevant foreign patent laws, for any working combination or some sub-combination of the features herein.

Moreover, the scope of the present application is not intended to be limited to the particular embodiments of the process, machine, manufacture, composition of matter, means, methods and steps described in the specification. As one of ordinary skill in the art will readily appreciate from the disclosure of the invention, processes, machines, manufacture, compositions of matter, means, methods, or steps, presently existing or later to be developed that perform substantially the same function or achieve substantially the same result as the corresponding embodiments described herein may be utilized according to the invention. Accordingly, the appended claims are intended to include within their scope such processes, machines, manufacture, compositions of matter, means, methods, or steps.

REFERENCE NUMERALS 101 video endoscope
103 handle
105 elongate shaft
107 proximal end of shaft
109 distal end of shaft
111 distal end section
113 cable
115 operator controls
201 display system
203 monitor
215 operators controls
301 objective system
303 lens system
305 front lens
307 rear lens
309 image sensor
311 optical filter (aperture)
313 outer ring
315 middle ring coating
317 inner ring coating
319 incidence light
323 white light beam
325 fluorescence beam
327 distal side
329 proximal side
335 aperture opening for ICG path
337 aperture opening for white light
339 cover glass
341 first lens (combined)
343 second lens (combined)
345 third lens
347 fourth lens
349 fluorescence filter
353 fifth lens (combined)
361 one-sided coated optical filter
363 black coating
365 reflecting coating
367 wide range coating
371 double-sided optical filter
373 optical axis
375 central region
377 peripheral region

The invention claimed is:

1. An optical filter for an objective system of a medical scope, wherein the optical filter comprises a light incident side and a light exit side, a central region around an optical axis and a peripheral region, wherein the optical filter is designed as an aperture with a single optical axis for white light and fluorescence light, wherein the optical filter comprises at least a first transmission zone for a transmittance of a first wavelength band and a second transmission zone for a transmittance of a second wavelength band, wherein at least one of the two transmission zones comprises a filter coating and the first wavelength band and the second wavelength band differ from each other, such that when both white light and fluorescence light are incident on the optical filter, a light beam cone of the fluorescence light emerging therefrom has a larger diameter than a light beam cone of the white light or vice versa.

2. The optical filter of claim 1, wherein the optical filter comprises a blocking zone, wherein the blocking zone is arranged at and/or in the peripheral region of the optical filter for blocking light of all wavelengths.

3. The optical filter of claim 2, wherein the first transmission zone, the second transmission zone or the blocking zone comprises a further filter coating.

4. The optical filter of claim 3, wherein the blocking zone comprises a black filter coating or is formed as a ring element at the light incident side.

5. The optical filter of claim 3, wherein the blocking zone comprises the further filter coating and has a transmission of less than 0.01% in the wavelength band of 350 nm to 1,100 nm.

6. The optical filter of claim 3, wherein the first transmission zone comprises the further filter coating and has a blocking of less than 2.5% in the wavelength band of 415 nm to 900 nm.

7. The optical filter of claim 2, wherein the blocking zone comprises a black filter coating or is formed as a ring element at the light incident side.

8. The optical filter of claim 2, wherein the respective filter coating is arranged on the light incident side and/or the light exit side.

9. The optical filter of claim 2, wherein the filter coating of the blocking zone comprises a transmission of less than 0.01% in the wavelength band of 350 nm to 1,100 nm.

10. The optical filter of claim 1, wherein the second transmission zone is arranged between the peripheral region and the central region of the optical filter for blocking white light and transmittance of fluorescence light.

11. The optical filter of claim 1, wherein the first transmission zone is arranged in the central region of the optical filter for transmittance of white light and/or fluorescence light.

12. The optical filter of claim 11, wherein the first transmission zone comprises the filter coating and has a blocking of less than 2.5% in the wavelength band of 415 nm to 900 nm.

13. The optical filter of claim 1, wherein the second transmission zone for transmittance of the second wavelength band comprises a F-number in a range between F/3.5 to F/4.5, and/or the first transmission zone for transmittance of the first wavelength band comprises a F-number in a range between F/5.5 to F/6.5.

14. The optical filter of claim 1, wherein the second transmission zone for transmittance of the second wavelength band comprises an outer diameter in a range between 0.85 mm to 1.25 mm and/or the first transmission zone for transmittance of the first wavelength band comprises an outer diameter in a range between 0.60 mm to 0.85 mm.

15. The optical filter of claim 1, wherein the second transmission zone comprises the filter coating and has a transmission of more than 98.0% in the wavelength band of 800 nm to 900 nm and a blocking of more than 99.5% in the wavelength band of 400 nm to 750 nm.

16. An objective system for an endoscope, wherein the objective system is arrangeable in a distal end section of an elongate shaft of the endoscope, wherein the objective system comprises a first lens, a second lens, and a third lens in order from an objective side to receive image light and to pass the image light towards a proximal side, wherein the objective system comprises one optical channel for white light and fluorescence light, wherein the objective system comprises an optical filter, wherein the optical filter comprises a light incident side and a light exit side, a central region around an optical axis and a peripheral region, wherein the optical filter is designed as an aperture with a single optical axis for white light and fluorescence light, wherein the optical filter comprises at least a first transmission zone for a transmittance of a first wavelength band and a second transmission zone for a transmittance of a second wavelength band, wherein at least one of the two transmission zones comprises a filter coating and the first wavelength band and the second wavelength band differ from each other, such that when both white light and fluorescence light are incident on the optical filter, a light beam cone of the fluorescence light emerging therefrom has a larger diameter than a light beam cone of the white light or vice versa.

17. The objective system of claim 16, wherein the objective system comprises a fluorescence filter for blocking an excitation wavelength, wherein the fluorescence filter is arranged on a proximal side of the optical filter within the objective system.

18. The objective system of claim 16, wherein the optical filter comprises a blocking zone, wherein the blocking zone is arranged at and/or in the peripheral region of the optical filter for blocking light of all wavelengths.

19. An endoscopic system, comprising an endoscope, a light source, and a display system, wherein the light source is configured to provide white light and fluorescence excitation light to a scene under observation with the endoscope; wherein the endoscope comprises a handle, an elongate shaft, an objective system, and at least one image sensor; and the objective system comprises a first lens, a second lens, and a third lens, and an optical filter, and wherein the optical filter comprises a light incident side and a light exit side, a central region around an optical axis and a peripheral region, wherein the optical filter is designed as an aperture with a single optical axis for white light and fluorescence light, wherein the optical filter further comprises at least a first transmission zone for a transmittance of a first wavelength band and a second transmission zone for a transmittance of a second wavelength band, wherein at least one of the two transmission zones comprises a filter coating and the first wavelength band and the second wavelength band differ from each other, such that, after passing through the objective system, white light and fluorescence light with different corresponding F-numbers may be captured by the at least one image sensor.

20. The endoscopic system of claim 19, configured such that a white light image and a fluorescence light image, captured by the at least one image sensor, are displayable, by means of the display system, with approximately the same resolution.

* * * * *